United States Patent [19]
Shimada et al.

[11] 4,137,161
[45] Jan. 30, 1979

[54] LIQUID CHROMATOGRAPH APPARATUS

[75] Inventors: Mitsuo Shimada; Yoshio Fujii, both of Ibaraki, Japan

[73] Assignee: Hitachi, Ltd., Tokyo, Japan

[21] Appl. No.: 763,673

[22] Filed: Jan. 28, 1977

[30] Foreign Application Priority Data

Jan. 30, 1976 [JP] Japan .................................. 51-8530

[51] Int. Cl.² ........................................... B01D 15/08
[52] U.S. Cl. ................................ 210/31 C; 73/61.1 C; 210/198 C
[58] Field of Search ............ 210/31 C, 198 C; 55/67, 55/197, 386; 73/23.1, 61.1 C

[56] References Cited

U.S. PATENT DOCUMENTS

| | | | |
|---|---|---|---|
| 3,068,686 | 12/1962 | Harmon | 55/386 X |
| 3,458,437 | 7/1969 | Ouono | 210/31 C |
| 3,981,179 | 9/1976 | Roof | 210/198 C |
| 4,016,074 | 4/1977 | Porter | 210/31 C |

*Primary Examiner*—John Adee
*Attorney, Agent, or Firm*—Thomas E. Beall, Jr.

[57] ABSTRACT

A detecting device is disposed between a separation column to which an eluent is supplied and a flow passage resisting member is located in a flow passage leading to a liquid discharge exit. This detecting device includes a sample cell and a reference cell. The effluent from the separation column is introduced into the flow passage resisting member through the sample cell. A change-over valve is disposed in the flow passage between the separation column and the sample cell and also is connected to one end of the reference cell. The other end of the reference cell is connected to the flow passage between the sample cell and the flow passage resisting member, whereby the reference cell and sample cell are kept communicated with each other.

After an eluent has been filled in the reference cell, the communication of the flow passage between the separation column and the sample cell with the reference cell is intercepted by the change-over valve. While this interception is maintained, an effluent from the separation column is passed through the sample cell, and concentrations of respective components in the sample solution are measured by comparing the sample solution with the reference solution in the reference cell with respect to the refractive index or absorbance. Since the noise and drift can be reduced according to this system, the measurement accuracy can be highly improved.

13 Claims, 8 Drawing Figures

LIQUID CHROMATOGRAPH APPARATUS

BACKGROUND OF THE INVENTION

The present invention relates to a liquid chromatograph apparatus. More particularly, the invention relates to a liquid chromatograph apparatus arranged so as to determine contents or concentrations of respective components of a sample solution by comparing the sample solution with a reference solution.

In a liquid chromatograph apparatus, an eluent is first introduced into a separation column, passed through a detecting device and then discharged. After passage through the detecting device, the eluent is discharged into open air through a flow passage resisting member. Since a finely particulate ion-exchange resin is packed in the separation column, a high pressure is imposed on the inlet side of the column. In many cases, a differential refractometer or beam absometric photometer is used as the detecting device. A sample cell and a reference cell are disposed in the detecting device. Luminous fluxes are radiated on each of these cells, and transmitted or reflected rays are taken and the solutions in the two cells are compared with respect to the absorbance or refractive index.

The environment is not always identical between the sample cell and the reference cell. More specifically, although the effluent from the separation column is continuously passed to the sample cell, the reference solution in the reference cell is kept stationary in a closed chamber. In general, the reference cell is disposed quite independently from the conduit system where the sample cell is located, and both the ends of the reference cell are closed at the time of measurement. Therefore, the pressure conditions differ between both the cells, and this pressure difference results in a measurement error.

There is known a liquid chromatograph apparatus in which separately from a separation column, a reference column is disposed in parallel to the separation column downstream of a pump so that an effluent from the reference column is continuously fed into the reference cell. In this known apparatus, the sample cell and reference cell are connected to each other in the upstream portions thereof through the two columns, but in the downstream portions, they are independent from each other. In this apparatus, the pressure difference can be moderated to some extent, but it cannot be said that the effect is sufficient. Moreover, since the eluent must be fed continuously to two column passages, the amount consumed of the eluent is twice as large as in the first mentioned liquid chromatograph apparatus, and the structure becomes complicate.

SUMMARY OF THE INVENTION

It is an object of the present invention to provide a liquid chromatograph apparatus in which the substantially same pressure is maintained in the sample cell and the reference cell.

Another object of the present invention is to provide a liquid chromatograph apparatus in which the noise can be remarkably reduced though the structure of the apparatus is very simple.

Still another object of the present invention is to provide a liquid chromatograph apparatus in which when the pressure in the sample cell is varied, the pressure in the reference cell is similarly varied so that the substantially same pressure is maintained in both the cells.

In accordance with the present invention, there is provided a liquid chromatograph apparatus wherein a sample cell is disposed between a flow passage resisting member and a separation column, both of which are located in a flow passage for taking out separated components, one of an inlet and an outlet of a reference cell is communicated with the flow passage between the separation column and the flow passage resisting member, and the other of the inlet and outlet of the reference cell is closed when a sample solution is passed through the sample cell.

DETAILED DESCRIPTION OF THE PREFERRED EMBODIMENTS

Figure 1:
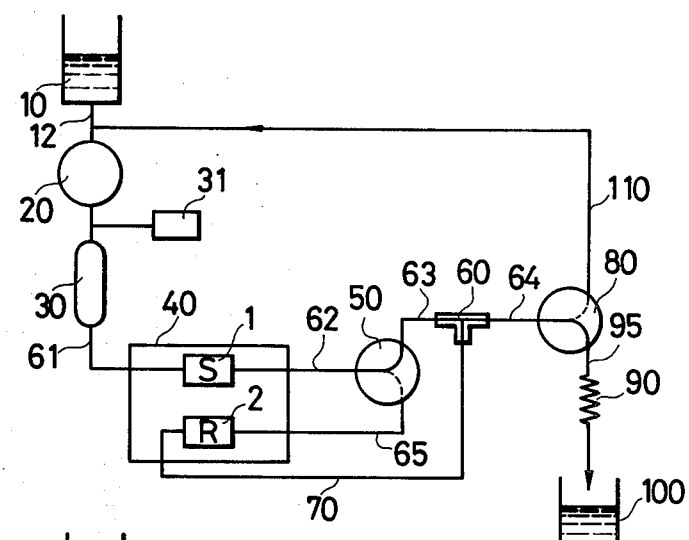
FIG. 1 is a diagram illustrating the outline of the structure of one embodiment of the liquid chromatograph apparatus of the present invention.

FIG. 1 illustrates one embodiment of the liquid chromatograph apparatus to which the present invention is applied. In the drawing, only one eluent tank 10 is shown, but in the practical operation, a plurality of eluent tanks 10 are provided and they are connected in succession to a liquid feed pump 20. The feed pump 20 is ordinarily constructed by combining a plurality of plunger type reciprocating pumps so as to reduce pulsating currents. For example, ion exchange resin particles are packed in a separation column 30. The kind of the filler to be packed in the separation column 30 is selected depending on the kind of the sample. A sample introducing device 31 is disposed to introduce a sample containing a plurality of components to the separation column 30. A detecting device 40 consists of, for example, a differential refractometer or absometric photometer, which includes a sample cell 1 and a reference cell 2. A sample-containing solution is passed into the sample cell 1 and a reference solution is contained in the reference cell 2. One flux of dual beams from a light source (not shown) is radiated on the sample cell 1 and the other flux is radiated on the reference cell 2. When the detecting device 40 is a differential refractometer, the sample cell and reference cell are disposed on the surface of a prism and the refractive indexes of both the solutions are compared with each other based on reflected rays, and as a result, the change of the refractive index owing to the sample is determined. When the detecting device 40 is an absometric photometer, rays transmitted through both the cells are compared with each other, and as a result, the change of the absorbance of a specific wave-length ray owing to the sample is determined. The measurement results are drawn as a chromatogram.

A flow passage resisting member 90 is disposed on a flow passage 95 for taking out separated components into a vessel 100. This flow passage resisting member 90 is disposed to apply a back pressure of about 2 atmospheres to the sample cell, and in general, it consists of a needle valve, a thin, long capillary tube, a tube packed with a filler, or the like. Because of provision of this resisting member 90, generation of bubbles in the effluent from the separation column can be prevented.

The sample cell 1 in the detecting device 40 is connected to an outlet of the separation column 30 through a flow passage 61, and it also is connected to a flow passage change-over valve 50 through a flow passage 62. This flow passage change over valve 50 is connected to a flow passage change-over valve 80 through a flow passage 63, a three-way tube 60 and a flow passage 64. One outlet of the flow passage change-over valve 80 is communicated with the flow passage 95 having the flow passage resisting member 90, and the other outlet is communicated through a recycle flow passage 110 with a flow passage 12 between the eluent tank 10 and the liquid feed pump 20. One of two outlets of the change-over valve 50 is connected to the reference cell 2 through a flow passage 65, and the reference cell 2 is communicated with the three-way tube 60 through a flow passage 70. The reference cell 2 and three-way tube 60 are always kept communicated with each other.

Prior to measurement of the sample, the flow passage change-over valve 50 is arranged so that the flow passage 62 is communicated with the flow passage 65, and the flow passage change-over valve 80 is arranged so that the flow passage 64 is communicated with the flow passage 95. In this state, the eluent is fed by the liquid feed pump 20 and is flown into the reference cell 2, the flow passage 65 and the flow passage 70 so that bubbles are not left in these members. Then, the flow passage change-over valve 50 is operated so that the flow passage 62 is communicated with the flow passage 63, and the eluent is flown continuously for a while until a stable base line is obtained. During this period, the flow passage change-over valve 80 may be adjusted so that the flow passage 64 is communicated with the recycle flow passage 110. In this state, the communication between the flow passages 62 and 65 is intercepted by the flow passage change-over valve 50, but the flow passage 65, reference cell 2 and flow passage 70 are filled with the eluent.

Then, a predetermined amount of a sample is introduced into the separation column 30 by means of the sample introducing device 31, and the sample which has been separated or fractionated into respective components by the column 30 is passed through the sample cell 1 and discharged into the vessel 100 through the flow passage change-over valves 50 and 80. A plurality of separated components pass through the sample cell 1 in succession, but the pressure is not always maintained at the same level in the sample cell while the components pass through the sample cell. In the present embodiment, however, since the interior of the reference cell 2 is communicated with the flow passage on the side of the sample cell 1 at the three-way tube 60, the pressure change in the sample cell 1 is directly transmitted to the interior of the reference cell 2 and the same liquid pressure is maintained in both the cells.

In the case where separation of components is insufficient when the sample solution is once passed through the separation column, the sample or a group of components are returned to the passage 12 through the recycle passage 110. Components separated when the sample is passed through the separation column 30 again can be taken out through the flow passage 95. The flow passage change-over valve 80 may be controlled so that the flow passage 64 is communicated with the flow passage 95 only when components separated from other components are passed through the separation column 30 repeatedly.

Figure 3:
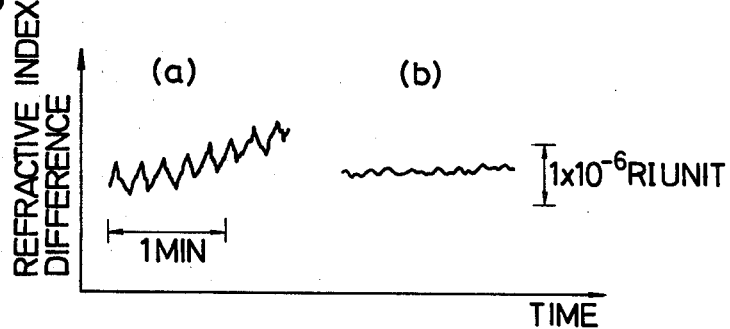
FIGS. 3 and 4 are graphs comparing base lines between the apparatus to which the present invention is applied and the apparatus to which the present invention is not applied.
Figure 4:
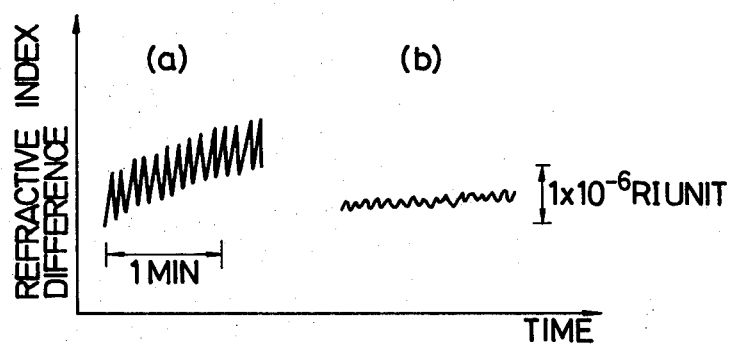

FIGS. 3 and 4 are diagrams comparing base lines obtained when another valve is disposed in the flow passage 70 in the chromatograph apparatus shown in FIG. 1 and the valve is closed [FIGS. 3-(a) and 4-(a)] with base lines obtained when said valve is opened [FIGS. 3-(b) and 4-(b)]. More specifically, base lines (a) are those obtained when the present invention is not applied and base lines (b) are those obtained when the present invention is applied. When the flow rate of the eluent is 1 ml/min as in FIG. 4, if the communication between the sample cell 1 and reference cell 2 is intercepted between the separation column 30 and the flow passage resisting member 90, the intensity of the noise is $1 \times 10^{-6}$ RI unit, whereas if the sample cell 1 and reference cell 2 are kept communicated with each other, the noise intensity is $2 \times 10^{-7}$ RI unit. Also when the flow rate of the eluent is 0.5 ml/min as in FIG. 3, the noise intensity is reduced to 1/5 by application of the present invention as in the case shown in FIG. 4, and simultaneously, the drift width can be remarkably improved. Similar results can be obtained when the change-over valve 80 in FIG. 1 is adjusted so that the flow passage 64 is kept communicated with the recycle passage 110.

Figure 2:
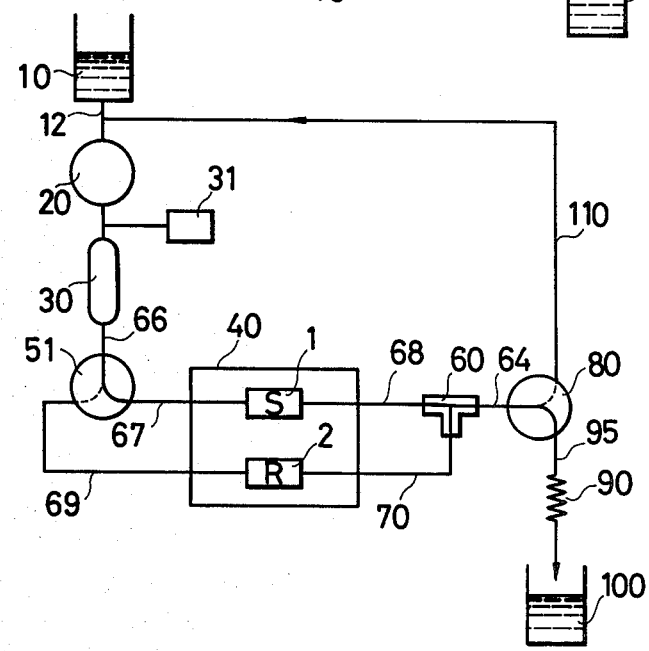
FIG. 2 is a diagram illustrating the outline of the structure of another embodiment of the liquid chromatograph apparatus of the present invention.

FIG. 2 illustrates the outline of the structure of another embodiment of the present invention. In this embodiment, the separation column 30 is connected to the sample cell 1 through a flow passage 66, a flow passage change-over valve 51 and a flow passage 67. The outlet of the sample cell 1 is connected to a three-way tube 60 through a flow passage 68. One of the inlet and outlet of the reference cell 2 is connected to the flow passage change-over valve 51 through a flow passage 69 and the other is connected to the three-way tube 60 through a flow passage 70. Members having the same functions as those of the members shown in FIG. 1 are represented by the same reference numerals.

Prior to introduction of a sample, an eluent is filled in the flow passage 69, reference cell 2 and flow passage 70 through the flow passage change-over valve 51. Then, the change-over valve 51 is operated so that the flow passage 66 is communicated with the flow passage 67. While the sample is being separated, the flow passage 66 is intercepted from the flow passage 69 by the change-over valve 51, but the sample cell 1 is kept communicated with the reference cell 2 by means of the three-way tube 60. Accordingly, the substantially same pressure is maintained in the two cells.

Figure 5:
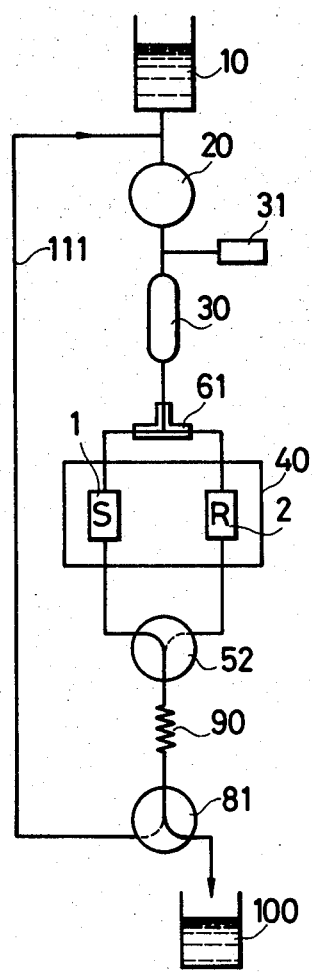
FIG. 5 is a diagram illustrating the outline of the structure of still another embodiment of the liquid chromatograph apparatus of the present invention.

In an embodiment illustrated in FIG. 5, a three-way tube 61 is disposed between the separation column 30 and the sample cell 1, and this three-way tube 61 is kept communicated also with the reference cell 2. Both the sample cell 1 and reference cell 2 are connected to a flow passage change-over valve 52. When the change-over valve 52 is operated so that the reference cell 2 is communicated with the flow passage resisting member 90, the eluent is filled in the reference cell 2, but when the change-over valve 52 is operated so that the sample cell 1 is communicated with the flow passage resisting member 90, the sample is separated. A flow passage change-over valve 81 is disposed so as to determine whether the separated sample is taken out of the system to the vessel 100 or returned to the liquid feed pump 20 through the recycle passage 111. In this embodiment, at the time of separation or analysis of the components of the sample, since the sample cell 1 is communicated with the reference cell 2 through the three-way tube 61, there is brought about no pressure difference between both the cells.

Figure 6:
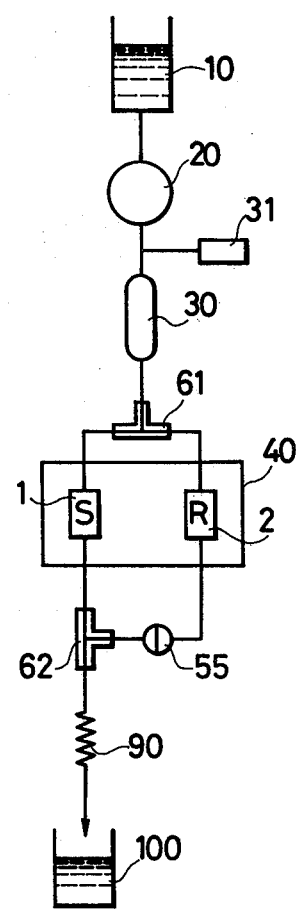
FIG. 6 is a diagram illustrating the outline of the structure of a further embodiment of the liquid chromatograph apparatus of the present invention.

In an embodiment shown in FIG. 6, the sample cell 1 and reference cell 2 are connected to the separation column 30 through a three-way tube 61, and another three-way tube 62 is disposed between the sample cell 1 and the flow passage resisting member 90 located in a flow passage for taking out separated components. A valve 55 is disposed between the reference cell 2 and the three-way tube 62. When the valve 55 is opened to pass the eluent, the eluent is passed from the tank 10 into both the sample cell 1 and reference cell 2, and is then discharged into the vessel 100 through the flow passage resisting member 90. If the valve 55 is then closed, the eluent is passed only through the sample cell 1, and the eluent is left in the reference cell 2. While the valve 55 is closed, the sample is separated and the separated components are analyzed by the detecting device 40. Even while the valve 55 is closed, the sample cell 1 is communicated with the reference cell 2 at the three-way tube 61. Accordingly, the substantially same pressure is maintained in both the cells, but the sample is passed through the sample cell 1 alone. Since the pressure in the conduit system between the separation column 30 and the flow passage resisting member 90 is kept higher than the atmospheric pressure by the presence of the resisting member 90, the change in the atmospheric pressure has no influence on the pressure in the cells 1 and 2.

Figure 7:
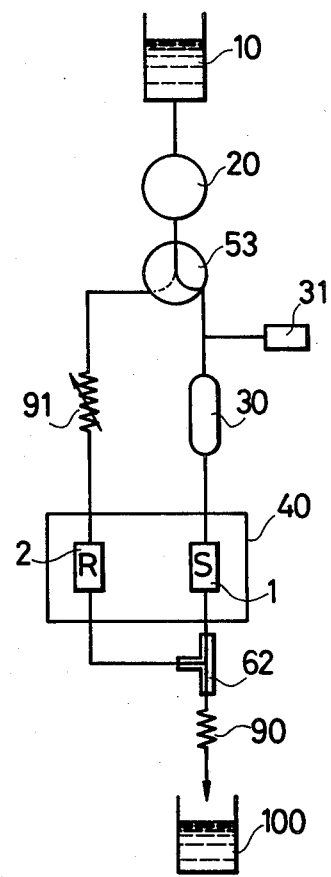
FIG. 7 is a diagram illustrating the outline of the structure of a still further embodiment of the liquid chromatograph apparatus of the present invention.

In an embodiment shown in FIG. 7, a flow passage change-over valve 53 is disposed between the liquid feed pump 20 and the separation column 30, and a three-way tube 62 is disposed between the sample cell 1 and the flow passage resisting member 90. In a by-pass flow passage between the flow passage change-over valve 53 and the three-way tube 62, there are disposed a variable flow passage resisting member 91 and the reference cell 2. In this embodiment, the flow passage change-over valve 53 for closing one of the inlet and outlet of the reference cell 2 is located upstream of the separation column 30. The three-way tube 62 communicating the sample cell 1 with the reference cell 2 is located between the separation column 30 and the flow passage resisting member 90.

Figure 8:
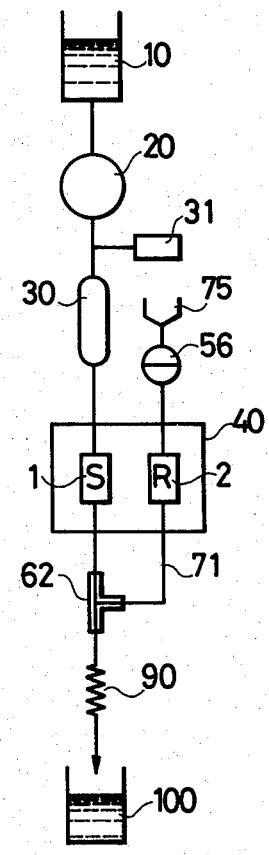
FIG. 8 is a diagram illustrating the outline of the structure of a still further embodiment of the liquid chromatograph apparatus of the present invention.

In an embodiment illustrated in FIG. 8, in the eluent passage, there are disposed the separation column 30, the sample cell 1, the three-way tube 62 and the flow passage resisting member 90, and in a branch passage 71 connected to the three-way tube 62, there are disposed the reference cell 2 of the detecting device 40, a valve 56 and a reference solution introducing member 75. A reference solution, which is the same as the eluent or is a different solution prepared especially, is contained in the reference solution introducing member 75. The valve 56 is opened to flow the reference solution through the branch passage 71 and expel air bubbles, and then, the valve 56 is closed to fill the reference solution in the reference cell 2. Since the sample cell 1 is communicated with the reference cell 2 through the three-way tube 62, the pressure change occuring in the sample cell 1 is directly transmitted to the reference cell 2. Namely, substantially same pressure changes are brought about in both the cells substantially instantaneously, and therefore, the measurement error caused by the pressure change can be cancelled.

What is claimed is:

1. A liquid chromatograph apparatus, comprising:
   a separation column having an inlet and an outlet, for separating a plurality of components contained in a sample to produce an effluent;
   means for feeding an eluent to the inlet of said separation column;
   a flow passage resisting member;
   detecting means including a sample cell and a reference cell, both having an inlet and outlet;
   passage means for receiving the effluent with separated components from the outlet of said separation column and passing the effluent in order through said sample cell and said flow resisting member;
   communicating means for directly fluid communicating without substantial resistance between one of the inlet and outlet of said reference cell with one of the inlet and outlet of said sample cell in said passage means between said separation column and said flow passage resisting member, to equalize the fluid pressure in the sample cell and reference cell; and
   closing means for closing the other of the inlet and outlet of said reference cell while the sample is being passed through said sample cell to conserve fluid.

2. A liquid chromatograph apparatus as set forth in claim 1 wherein said detecting means is a differential refractometer.

3. A liquid chromatograph apparatus as set forth in claim 1 wherein said detecting means is an absometric photometer.

4. A liquid chromatograph apparatus as set forth in claim 1 wherein said communicating means is passage means for connecting said reference cell with the flow passage between said sample cell and said flow passage resisting member.

5. A liquid chromatograph apparatus as set forth in claim 4 wherein said closing means is a change-over valve disposed in the flow passage between said sample cell and said flow passage resisting member and connected to said reference cell.

6. A liquid chromatograph apparatus as set forth in claim 4 wherein said closing means is a change-over valve disposed in the flow passage between said separation column and said sample cell and connected to said reference cell.

7. A liquid chromatograph apparatus as set forth in claim 4 wherein said closing means is a change-over valve disposed in the flow passage between said eluent feed means and said separation column and connected to said reference cell.

8. A liquid chromatograph apparatus as set forth in claim 4 wherein said closing means is a valve connected to said reference cell.

9. A liquid chromatograph apparatus as set forth in claim 1 wherein said communicating means is passage means for connecting said reference to the flow passage between said separation column and said sample cell.

10. A liquid chromatograph apparatus as set forth in claim 9 wherein said closing means is a change-over valve disposed in the flow passage between said sample cell and said flow passage resisting member and connected to said reference cell.

11. A liquid chromatograph apparatus as set forth in claim 9 wherein said closing means is a valve disposed in the flow passage between said sample cell and said flow passage resisting member and connected to said reference cell.

12. A liquid chromatograph apparatus comprising a separation column for separating a plurality of components contained in a sample, means for feeding an eluent to said separation column, detecting means including a sample cell and a reference cell, passage means for introducing an effluent from said separation column toward a liquid discharge exit through said sample cell, means for providing a resistance in said passage means to a fluid flow of the effluent downstream of said sample cell, recycle means for returning the effluent from said passage means toward said feeding means, means for communicating one of an inlet and outlet of said reference cell to said passage means between said separation column and said resistance providing means, and means for closing the other of the inlet and outlet of said reference cell while the sample is being passed through said sample cell.

13. A liquid chromatograph method, comprising the steps of: passing a liquid through a reference cell of a detector to clear the reference cell of gas bubbles; closing one of an inlet and outlet of said reference cell while the liquid is filled in said reference cell; maintaining direct fluid communication between a sample cell of said detector and the other of said inlet and outlet of said reference cell to maintain substantially identical pressures in said sample cell and said reference cell while simultaneously providing a resistance to a fluid flow of an effluent from said sample cell to provide the same back pressure to both said sample cell and said reference cell and isolate said sample cell and said reference cell from changes in atmospheric pressure; passing an eluent with a sample therein through a separation column to separate the sample into its components; thereafter passing the eluent from said separation column with the separated components of the sample therein through said sample cell during said steps of maintaining and providing; and passing light rays through said reference cell with its contained liquid and said sample cell as the separated sample passes therethrough and measuring the effect upon the light rays of said reference cell and sample cell, respectively.

* * * * *